United States Patent
McKinley

(10) Patent No.: US 7,615,053 B2
(45) Date of Patent: Nov. 10, 2009

(54) SURGICAL RONGEUR

(75) Inventor: Laurence M. McKinley, Escondido, CA (US)

(73) Assignee: Aeolin, LLC, Escondido, CA (US)

( * ) Notice: Subject to any disclaimer, the term of this patent is extended or adjusted under 35 U.S.C. 154(b) by 644 days.

(21) Appl. No.: 11/005,058

(22) Filed: Dec. 6, 2004

(65) Prior Publication Data

US 2006/0122615 A1 Jun. 8, 2006

(51) Int. Cl.
*A61B 17/00* (2006.01)

(52) U.S. Cl. .......................................... 606/83

(58) Field of Classification Search ................ 606/83, 606/79, 170, 174, 205, 184, 167, 171; 600/564
See application file for complete search history.

(56) References Cited

U.S. PATENT DOCUMENTS

| | | | |
|---|---|---|---|
| 5,201,739 A * | 4/1993 | Semm ........................ | 606/106 |
| 5,385,570 A * | 1/1995 | Chin et al. .................. | 606/170 |
| 5,582,618 A | 12/1996 | Chin et al. | |
| 5,618,294 A | 4/1997 | Aust et al. | |
| 5,653,713 A | 8/1997 | Michelson | |
| 5,662,656 A | 9/1997 | White | |
| 5,681,337 A | 10/1997 | Bray Jr. | |
| 5,683,406 A | 11/1997 | Altobelli et al. | |
| 5,702,420 A * | 12/1997 | Sterling et al. ............. | 606/205 |
| 5,718,714 A | 2/1998 | Livneh | |
| 5,766,177 A * | 6/1998 | Lucas-Dean et al. ........ | 606/83 |
| 5,795,291 A | 8/1998 | Koros et al. | |
| 5,961,531 A | 10/1999 | Weber et al. | |
| 6,142,997 A * | 11/2000 | Michelson ................... | 606/83 |
| 6,152,871 A | 11/2000 | Foley et al. | |
| 6,162,170 A | 12/2000 | Foley et al. | |
| 6,200,320 B1 | 3/2001 | Michelson | |
| 6,206,822 B1 | 3/2001 | Foley et al. | |
| 6,214,010 B1 | 4/2001 | Farley et al. | |
| 6,217,509 B1 | 4/2001 | Foley et al. | |
| 6,283,966 B1 | 9/2001 | Houfburg | |
| 6,425,859 B1 | 7/2002 | Foley et al. | |

(Continued)

OTHER PUBLICATIONS

International Search Report for International Application No. PCT/US2005/027458, International filing date Aug. 2, 2005, report completed Aug. 14, 2006, mailed Oct. 23, 2006, 2 pgs.

(Continued)

*Primary Examiner*—Pedro Philogene
(74) *Attorney, Agent, or Firm*—Kauth, Pomeroy, Peck & Bailey LLP

(57) ABSTRACT

A surgical rongeur for cutting bone or tissue is provided. The rongeur has an elongated track member, and a generally hollow cutting slide defining an inner cavity slidably received within the track member. The distal end of the cutting slide terminates in a sharp cutting edge and an opening. The distal end of the track member terminates in a foot plate. The cutting slide is longitudinally movable relative to the track member from a first open position to a second closed position. In the first open position, there is an opening between the sharp cutting edge and the foot plate, in which opening the bone to be cut is placed. In the second closed position the sharp cutting edge contacts the foot plate, cuts the bone and pushes the bone chip through the opening into the inner cavity of the cutting slide, where multiple bone chips may be stored.

35 Claims, 9 Drawing Sheets

U.S. PATENT DOCUMENTS

| | | | |
|---|---|---|---|
| 6,517,545 B1 | 2/2003 | Mazur | |
| 6,575,977 B1 * | 6/2003 | Michelson | 606/83 |
| 6,635,060 B2 | 10/2003 | Hanson et al. | |
| RE38,335 E | 11/2003 | Aust et al. | |
| 6,641,582 B1 | 11/2003 | Hanson et al. | |
| 6,679,833 B2 | 1/2004 | Smith et al. | |
| 6,685,710 B2 * | 2/2004 | Agbodoe et al. | 606/83 |
| 6,695,849 B2 | 2/2004 | Michelson | |
| 6,702,820 B2 | 3/2004 | Mazur | |
| 6,723,103 B2 | 4/2004 | Edwards | |
| 6,755,837 B2 | 6/2004 | Ebner | |

OTHER PUBLICATIONS

International Search Report for International Application No. PCT/US2005/027458, International filing date Aug. 2, 2005, Opinion completed Aug. 14, 2006, mailed Oct. 23, 2006, 3 pgs.

* cited by examiner

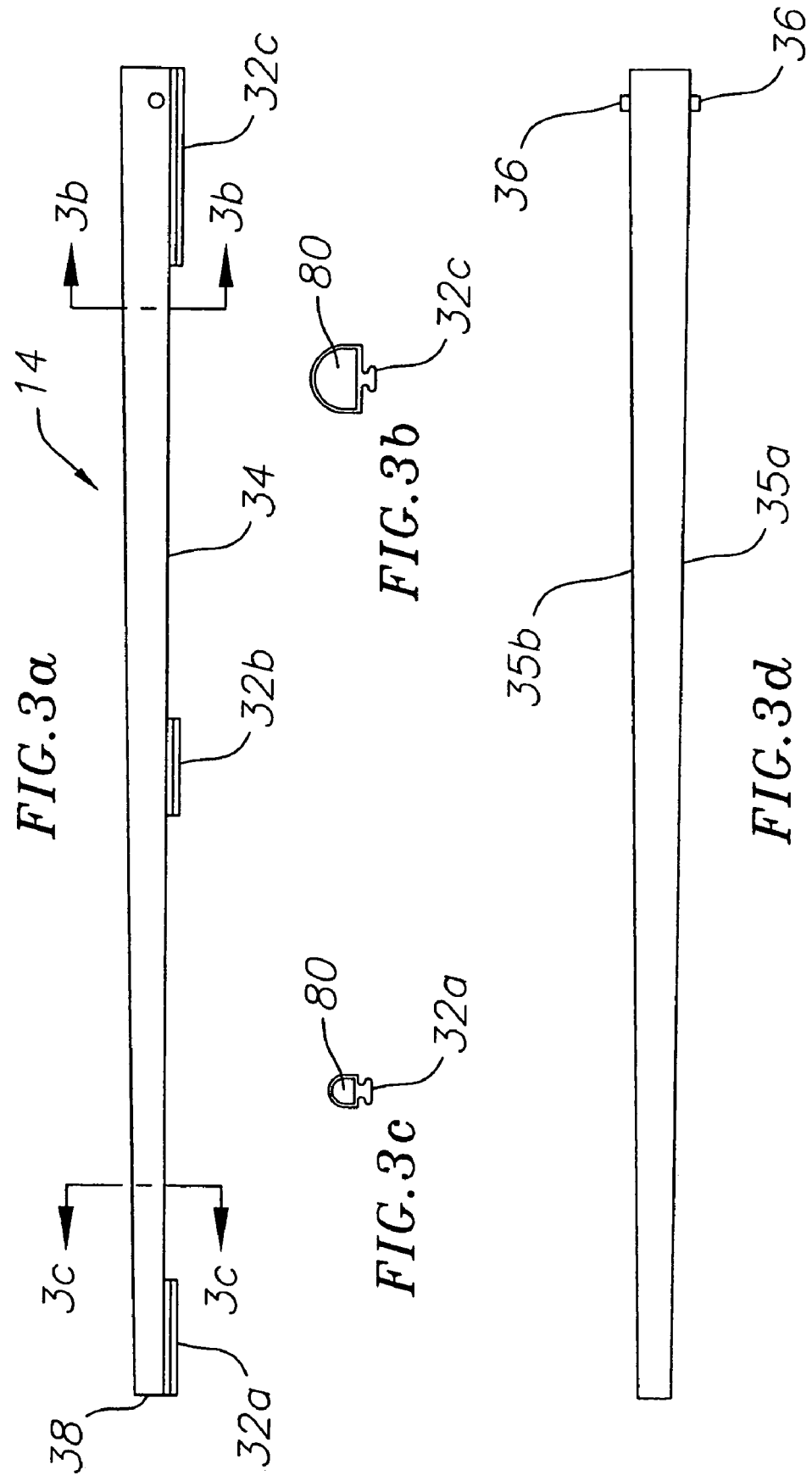

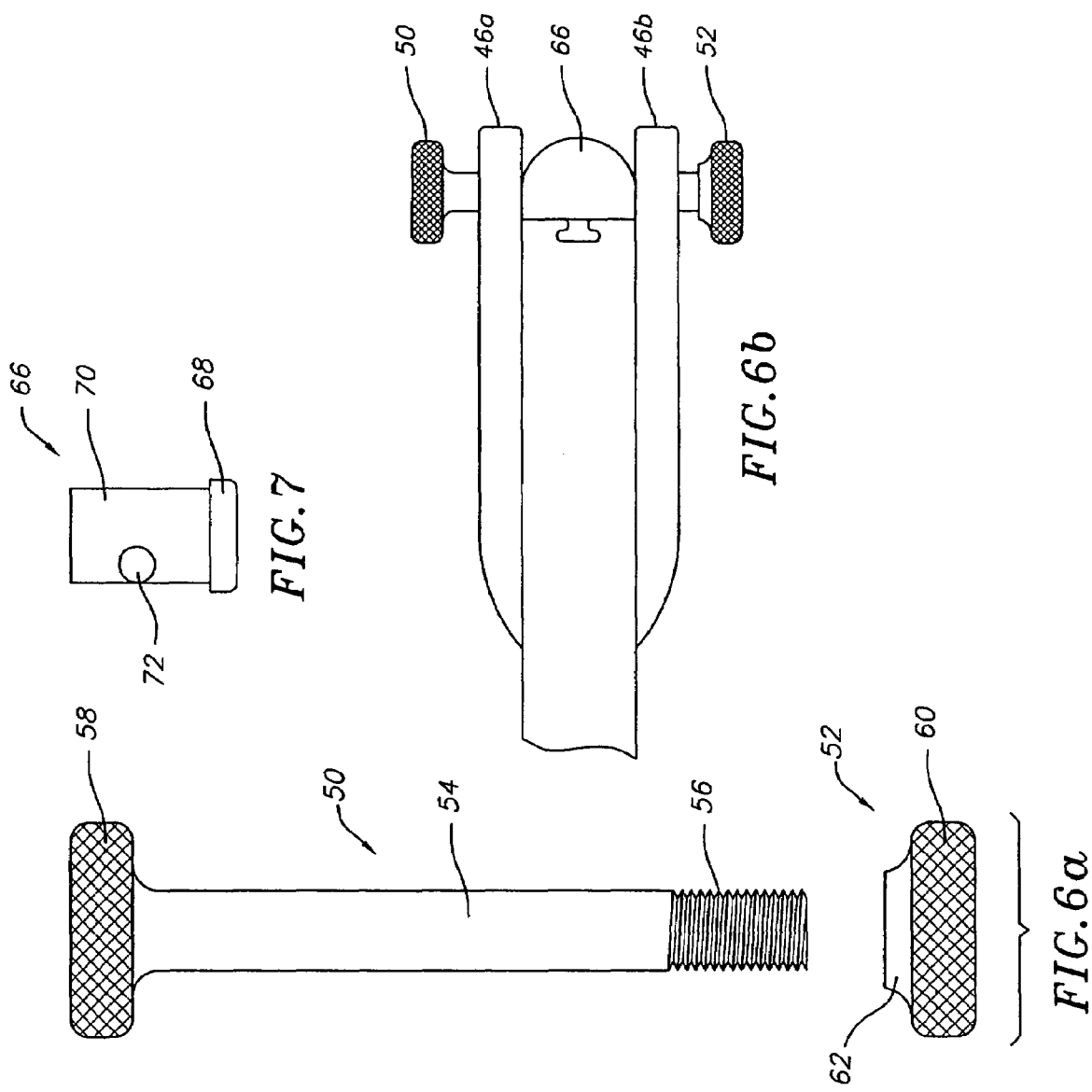

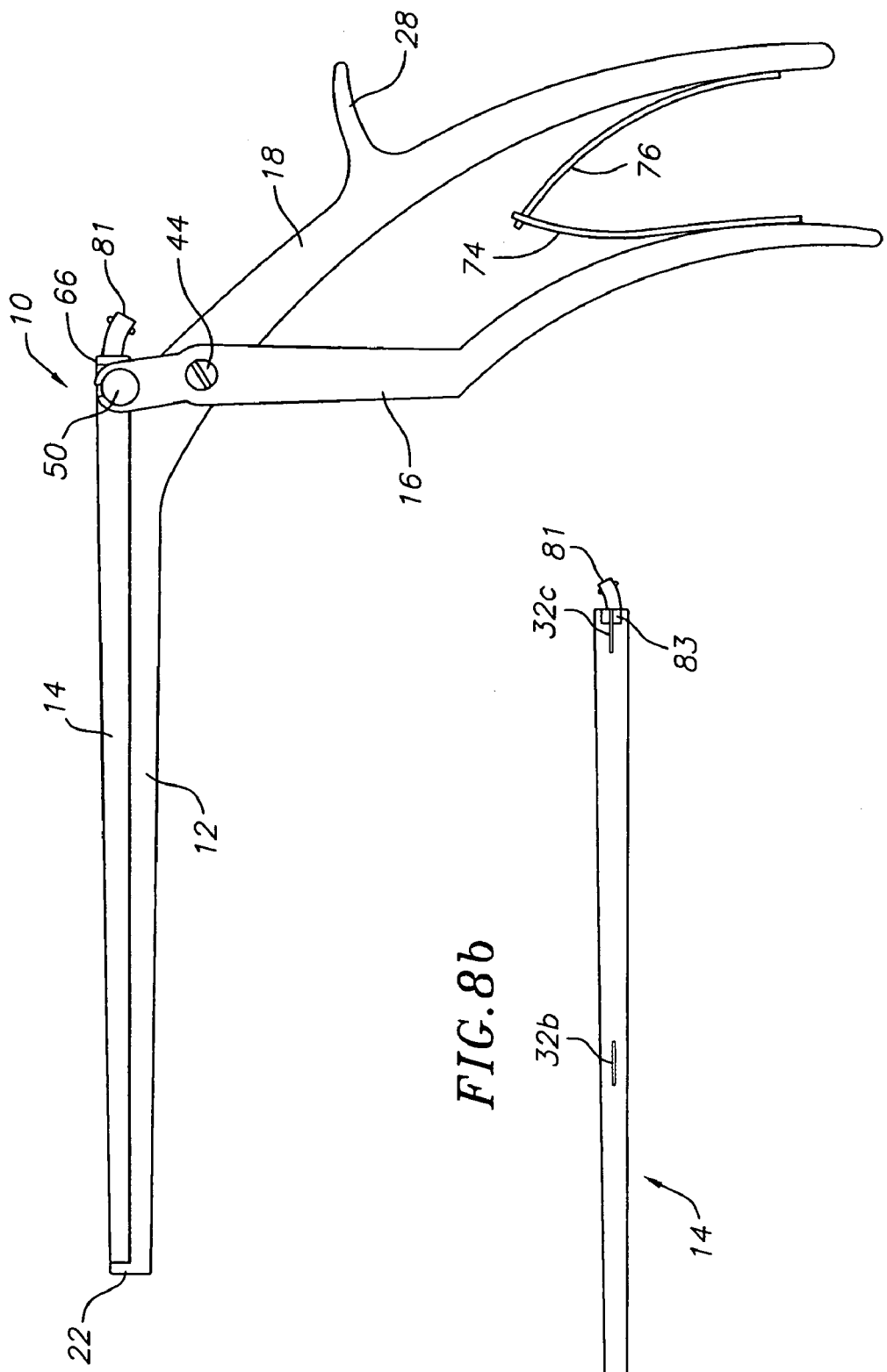

SURGICAL RONGEUR

FIELD OF THE INVENTION

The present invention relates to surgical rongeurs for cutting bone and other tissue, and more specifically to Kerrison-type surgical rongeurs used in laminectomies and laminotomies.

BACKGROUND OF THE INVENTION

Surgical rongeurs are well known in the surgical community. The Kerrison-type surgical rongeur is commonly used to cut bone and soft tissue. The Kerrison rongeur typically comprises a stationary shaft and a cutting slide that is longitudinally slidable relative to the stationary shaft. At the distal end of the cutting slide is a cutting edge which engages a foot plate that is located at the distal end of the stationary shaft. The cutting edge on the cutting slide and the foot plate on the stationary shaft are commonly referred to as the "cutting jaws".

Presently, Kerrison rongeurs include a small cup between the cutting jaws for capturing the cut pieces of bone. However, this cup can only hold a single bone chip. Consequently, the rongeur must be removed from the surgical site after each cut of bone in order to clean out the bone from the cup. To remove the bone from the cup, the surgeon often has his assistant clean out the bone from the cup with a small piece of cloth. However, if the bone is too tightly lodged in the cup, the surgeon relinquishes the rongeur to a scrub nurse who attempts to remove the bone using a knife or other instrument. The removal of the rongeur from the surgical situs and relinquishment of the rongeur to the nurse after each cut of bone greatly increases the amount of time necessary to complete the surgical task.

When the rongeur becomes old, the cutting edge becomes dull. Under these circumstances, the cutting edge is often advanced against the foot plate using force in excess of that necessary to cut the bone. When this occurs, the bone placed between the cutting jaws may become compacted in the cup and very difficult, often impossible, to remove without complete disassembly of the rongeur. The compacted bone, therefore, prevents any subsequent use of the rongeur. Also, the bone is often crushed rather than cut, creating added stress on the cutting jaws of the ronguer.

Also, the cutting edge on the cutting slide becomes dull over time, considerably decreasing the effectiveness of the rongeur. To compensate for the dull cutting edge, surgeons apply increasing force when advancing the cutting edge against the foot plate. This increased force causes the track receiving the cutting slide to stretch, and the cutting slide to thereby move upward against the foot plate. The upward movement of the cutting slide results in very poor cutting.

When the cutting becomes too poor, hospitals routinely send the rongeur to be sharpened. Because rongeurs are less expensive to sharpen than replace, hospitals will almost always first send the rongeur to be sharpened before replacing it. However, sharpening rarely helps the quality of the cutting, and hospitals generally replace the entire rongeur shortly thereafter. Consequently, hospitals typically spend far more to replace an ineffective rongeur than the cost of a new rongeur.

The replacement of the entire rongeur is generally necessary after they have become ineffective because rongeurs are typically constructed as a unitary instrument. However, because a rongeur typically becomes ineffective when the cutting edge becomes dull, only the replacement of the cutting edge is truly necessary. Therefore, a need arises for a rongeur with a removable and replaceable cutting edge.

Accordingly, a need exists for an improved surgical rongeur capable of increased efficiency and decreased expense.

SUMMARY OF THE INVENTION

The present invention is directed to a surgical rongeur for cutting bone and other tissue generally including an elongated track member, an elongated cutting slide, a support handle and a pivot handle, where the elongated track member includes a track running substantially the length of the elongated track member, which slidably receives the cutting slide.

In one embodiment, the distal end of the elongated track member terminates in a foot plate extending upwardly from the track member at an angle ranging from about 30° to about 100°, and the proximal end of the track member terminates in the support handle, which extends downwardly from the track member.

In another embodiment, the elongated cutting slide is generally hollow, defines an inner cavity, and terminates at its distal end in a sharp cutting edge and an opening. In such an embodiment, the sharp cutting edge is used to cut bone or tissue against the foot plate at the distal end of the elongated track member. Once the bone is cut, the foot plate pushes the bone fragment through the opening in the distal end of the cutting slide and into the inner cavity.

In yet another embodiment, the inner cavity of the cutting slide may store multiple bone chips, eliminating the need to remove a bone chip from the rongeur before performing another cut.

In still another embodiment, the cutting slide is completely removable from the rongeur and is replaceable.

In still another embodiment, the pivot handle controls the movement of the cutting slide relative to the track member. In such an embodiment, suitable manipulation of the pivot handle moves the cutting slide longitudinally relative to the track member from a first open position, to a second closed position. In the first position, the sharp cutting edge at the distal end of the cutting slide is positioned proximate to the foot plate at the distal end of the track member, defining an opening between the sharp cutting edge and the foot plate. The bone fragment intended to be cut is placed in the opening between the sharp cutting edge and the foot plate. In the second position, the sharp cutting edge is in contact with the foot plate, thereby cutting the bone fragment lying between the sharp cutting edge and the foot plate.

In yet another embodiment, a suction device is attached to the proximal end of the cutting slide. The suction device enables the progression of soft tissue through the interior of the cutting slide.

BRIEF DESCRIPTION OF THE DRAWINGS

These and other features and advantages of various embodiments of the present invention will be better understood by reference to the following detailed description when considered in conjunction with the following drawings wherein:

FIG. 2b is a side view of the elongated track member depicted in FIG. 2a;

FIG. 2c is a cross-sectional view of the elongated track member depicted in FIG. 2a;

FIG. 3a is side view of an elongated cutting slide constructed in accordance with an exemplary embodiment of the invention;

FIG. 3b is a cross-sectional view of the distal end of the elongated cutting slide depicted in FIG. 3a;

FIG. 3c is a cross-sectional view of the proximal end of the elongated cutting slide depicted in FIG. 3a;

FIG. 3d is a top view of the elongated cutting slide depicted in FIG. 3a;

FIG. 5b is a front view of the pivot handle depicted in FIG. 5a;

FIG. 6a is a schematic depicting a screw and bolt mechanism according to an exemplary embodiment of the invention;

FIG. 6b is a top view of the connection of the screw and bolt mechanism of FIG. 6a to the pivot handle of FIG. 5b, and the cutting slide of FIG. 3a;

FIG. 7 is a side view of a closure device constructed in accordance with an exemplary embodiment of the invention;

FIG. 8a is a side view of a surgical rongeur according to another exemplary embodiment, depicting the attachment of a suction device;

FIG. 8b is a bottom view of a cutting slide, depicting the suction device of FIG. 8a;

FIG. 9b is a side view of a rod for use with the tubing of FIG. 9a;

DETAILED DESCRIPTION OF THE INVENTION

Figure 1A:
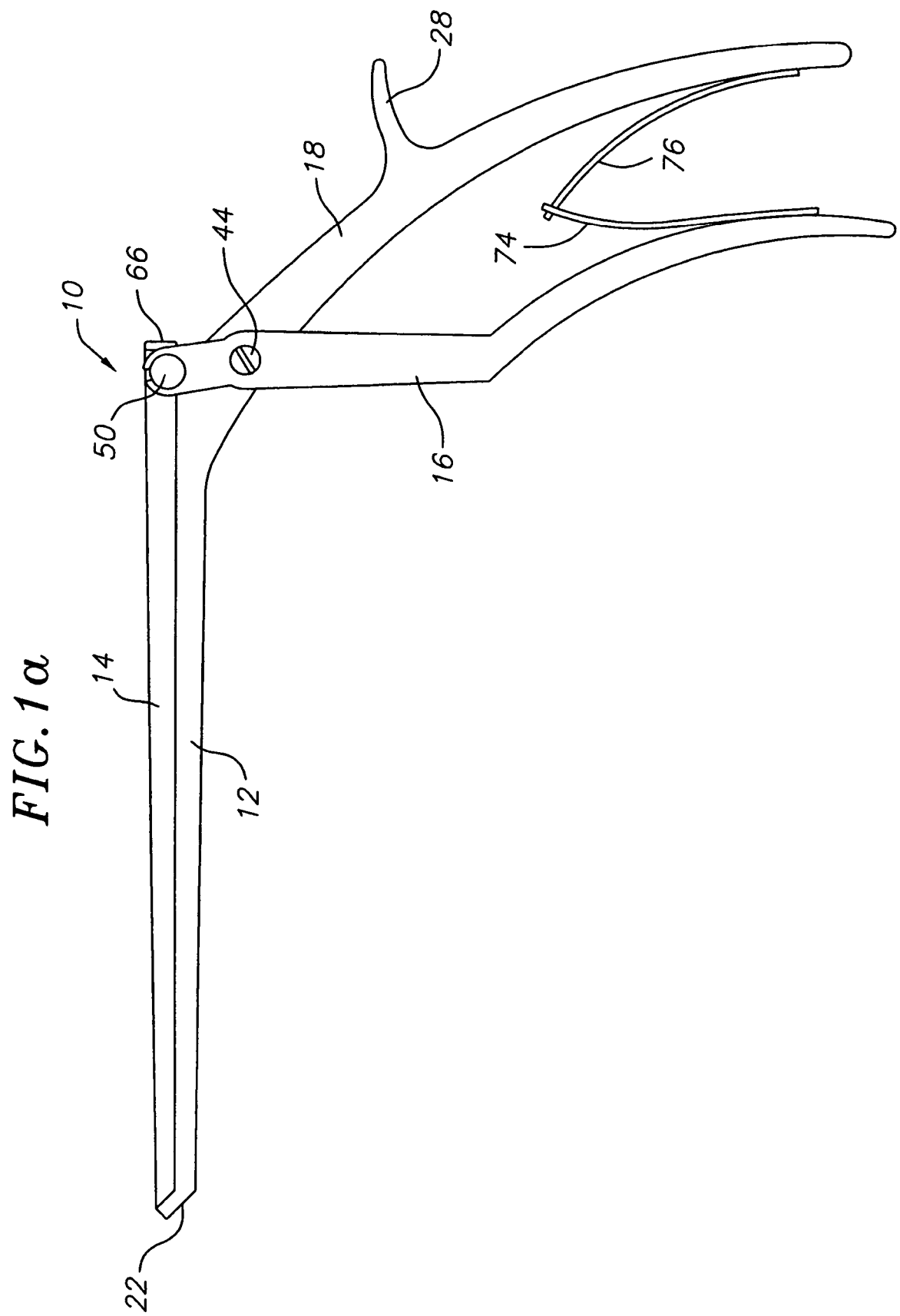
FIG. 1a is a side view of a surgical rongeur according to one exemplary embodiment of the invention in a first position.

The present invention is directed to a surgical rongeur for cutting bone and other tissue. The described exemplary embodiments of the rongeur of the present invention enable a surgeon to make and store multiple cuts of bone or other tissue without having to remove the rongeur from the surgical situs. In addition, the removable and replaceable cutting slide used with this rongeur can eliminate the need for costly, often ineffective, sharpening services.

In an exemplary embodiment, shown in FIG. 1, a surgical rongeur 10 generally includes an elongated track member 12 having proximal and distal ends and a longitudinal axis, a removable elongated cutting slide 14 having proximal and distal ends, a pivot handle 16 and a support handle 18. The distal end of the elongated track member 12 terminates in a foot plate 22 which extends upwardly from, and approximately perpendicularly to, the elongated track member 12. The foot plate 22 extends upwardly for a length approximately equal to the height of the distal end of the cutting slide 14. The foot plate 22 may be of any thickness sufficient to withstand the force exerted by the advancement of the cutting slide 14 against the foot plate 22. Although the footplate 22 is shown as being perpendicular to the track member 12 in the current embodiment, it should be understood that the foot plate 22 may extend upwardly in the distal direction at any desired angle, such as at an angle ranging from about 30° to about 100°, and preferably at an angle of about 45° relative to the longitudinal axis of the track member 12.

Figure 2A:
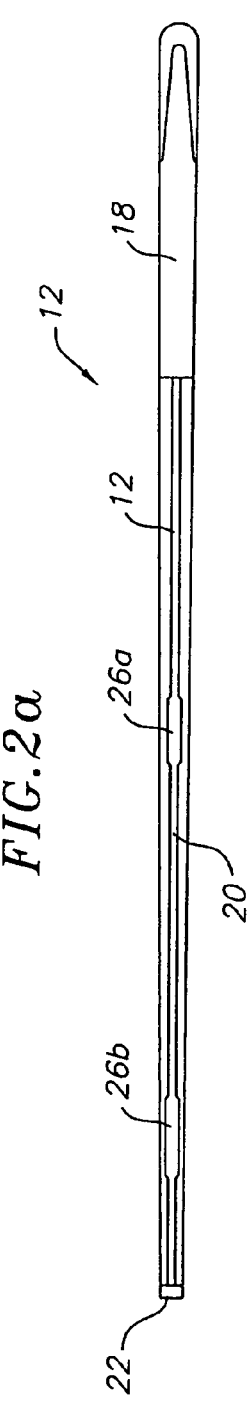
FIG. 2a is a top view of an elongated track member constructed in accordance with an exemplary embodiment of the invention.

As shown in FIG. 2a, the elongated track member 12 includes a track 20 for slidably receiving the elongated cutting slide 14 which extends approximately the length of the elongated track member 12. The track 20 serves to slidably receive the cutting slide 14 as described in more detail below. In the embodiment shown in FIG. 2a, the track 20 comprises an elongated narrow groove 24 in the top surface of the track member 12. However, the track 20 may comprise any suitable configuration such that the cutting slide 14 is slidably received within the track 20. Although the narrow groove 24 is generally T-shaped in the embodiment as shown in FIG. 2c, it should be understood that any cross section capable of slidably retaining the cutting slide may be utilized in the current invention. Along the length of the narrow groove 24 are two slots 26a and 26b having widths greater than the width of the narrow groove 24. In the embodiment shown in FIG. 2a, the first slot 26a is located between the mid-section and the proximal end of the elongated track member 12, and the second slot 26b is located near the distal end of the elongated track member 12, between the distal end and the mid-section. However, it should be understood that the two slots 26a and 26b may be of any design such that they are sufficiently wide and sufficiently long to facilitate the removal of the elongated cutting slide 14 from the track 20, as described in more detail below.

Figure 2B:
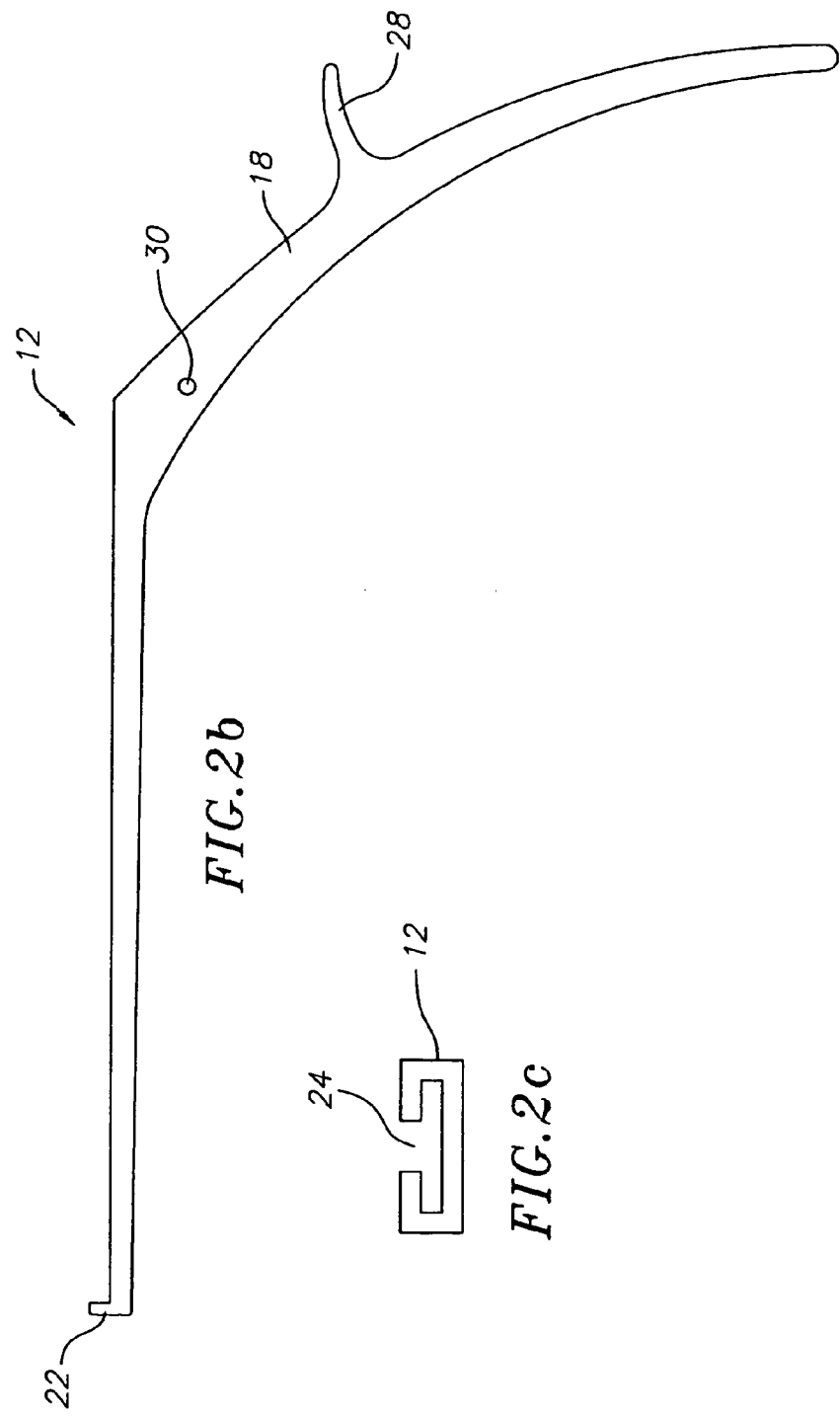
Figure 2C:
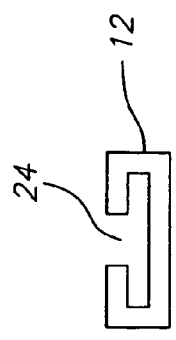

As shown in FIG. 2b, the proximal end of the elongated track member 12 terminates in the support handle 18. The support handle 18 has top and bottom ends and extends downwardly at an angle from the elongated track member 12. The support handle 18 may extend downwardly from the elongated track member 12 at any angle and to any length suitable to provide a comfortable grip on the support handle 18 when it is connected to the pivot handle 16. In this embodiment, the support handle 18 extends downwardly from the elongated track member 12 at an angle greater than 90°, and is generally curved in the direction of the distal end of the elongated track member 12. In the embodiment shown in FIG. 2b extending outwardly from about the midpoint of the support handle 18 is a thumb spike 28. The thumb spike 28 may be optionally included to enhance the grip on the support handle 18 by providing support for the area of the gripping hand between the thumb and the index finger.

Near the top end of the support handle 18 is an aperture 30. The aperture 30 is the point of attachment of the pivot handle 16 to the support handle 18, and defines the pivot point around which the pivot handle 16 pivots in order to effect movement of the elongated cutting slide 14. The pivot handle 16 may be attached to the support handle 18 by any means suitable to allow the pivot handle 16 to pivot about the pivot point defined by the aperture 30 in the support handle 18, e.g. a pivot pin, as described in more detail below.

The elongated cutting slide 14, as depicted in FIGS. 3a through 3d, is generally hollow, and defines an inner cavity 80. As shown in FIG. 3d, the first 35a and second 35b sides of the cutting slide 14 each carry an aperture 36 located near the bottom surface 34 of the proximal end of the cutting slide 14. The apertures 36 define the point of connection of the cutting slide 14 to the pivot handle 16. The pivot handle 16 may be connected to the cutting slide 14 by any suitable means, e.g. a screw and bolt mechanism, as described below.

In one embodiment, the inner cavity 80 of the cutting slide 14 is capable of storing multiple bone chips, eliminating the need to remove a bone chip before making each cut. The cutting slide 14 preferably increases in cross-sectional area from its distal to its proximal end, enabling bone chips to move proximally within the inner cavity 80 of the cutting slide 14 as successive bone chips are cut, proximally displacing the preceding bone chips. Accordingly, the distal end of the cutting slide 14 defines an opening (not shown) through which the cut bone chips pass to enter the inner cavity 80 of the cutting slide 14. The distal end of the cutting slide 14 is of sufficient height to permit passage of bone chips through the opening and into the inner cavity 80. The distal end of the cutting slide 14 also defines a sharp cutting edge 38. The sharp cutting edge 38 is used to cut the bone against the foot plate 22 when the surgical rongeur is assembled. Therefore, the sharp cutting edge 38 at the distal end of the cutting slide 14 is angled to match the angle of the foot plate 22 relative to the elongated track member 12, such that the entire surface of the cutting edge 38 is in contact with the entire surface of the foot plate 22 at the completion of a cut. Alternatively, the cutting edge may be convexly shaped to facilitate the removal of foraminal bone. During operation, once the bone is cut against the foot plate 22 with the cutting edge 38, the foot plate 22 pushes the bone fragment through the opening in the distal end of the cutting slide 14 toward the proximal end of the cutting slide 14 and into the inner cavity 80.

Figure 4:
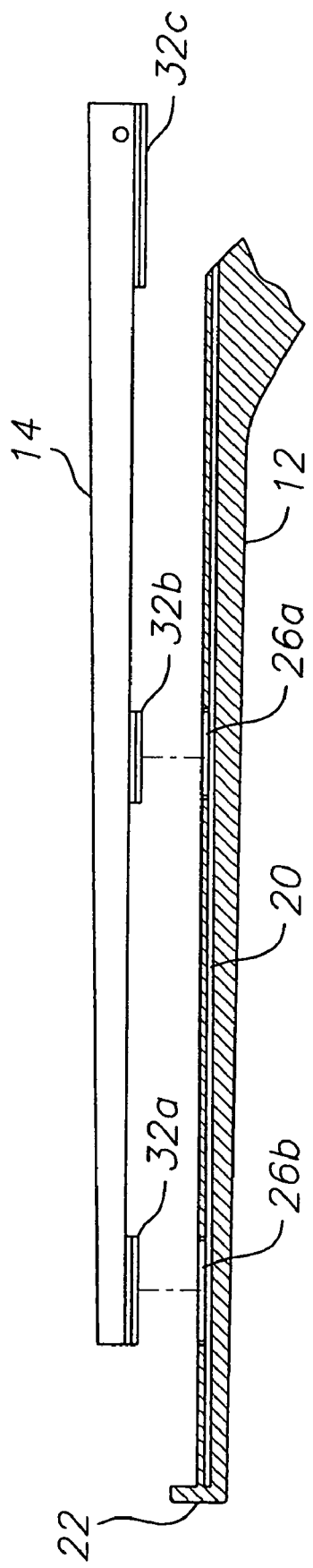
FIG. 4 is a longitudinal cross-sectional view of the alignment of the elongated cutting slide of FIG. 3a, and the elongated track member of FIG. 2a in a position for removing the cutting slide from the track member.

Extending downwardly from the bottom surface 34 of the cutting slide 14 are three track engaging protrusions 32a, 32b, and 32c. As shown in FIGS. 3b and 3c, in one embodiment, the track engaging protrusions 32a, 32b, and 32c are generally T-shaped for engaging the T-shaped groove 24 in the track 20 of the elongated track member 12; however, any suitable corresponding cross sections may be used such that the cutting slide may be slidably received by the extended track. In addition, as shown in the exemplary embodiment of FIGS. 3b and 3c, the first track engaging protrusion 32a is located at the distal end of the cutting slide 14 and is slightly shorter in length than the second slot 26b in the track 20 of the elongated track member 12, the second track engaging protrusion 32b is located at about the midpoint of the elongated cutting slide 14 and is slightly shorter in length than the first slot 26a in the track 20 of the elongated track member 12, and the third track engaging protrusion 32c is located at the proximal end of the elongated cutting slide 14 and is slightly longer than the other two track engaging protrusions 32a and 32b. In this embodiment, the protrusions 32a and 32b are sufficiently shorter than the slots 26a and 26b such that when the protrusions are aligned with the slots the protrusions may be lifted out of the track. In addition, the third track engaging protrusion 32c is sufficiently short such that when the first track engaging protrusion 32a is aligned with the second slot 26b, and the second track engaging protrusion 32b is aligned with the first slot 26a of the track 20, the third track engaging protrusion 32c lies completely outside the proximal end of the track 20. In this configuration, shown in FIG. 4, the first and second track engaging protrusions 32a and 32b may be lifted out of the second and first slots 26b and 26a, respectively, and the cutting slide may thereby be completely removed from the elongated track member 12. Despite the arrangement of slots and protrusions in this exemplary embodiment, it should be understood that any arrangement of protrusions and slots, or any other suitable configurations for the cutting slide 14 may be used such that the cutting slide 14 may be removably engaged with the track member 12.

Figure 5A:
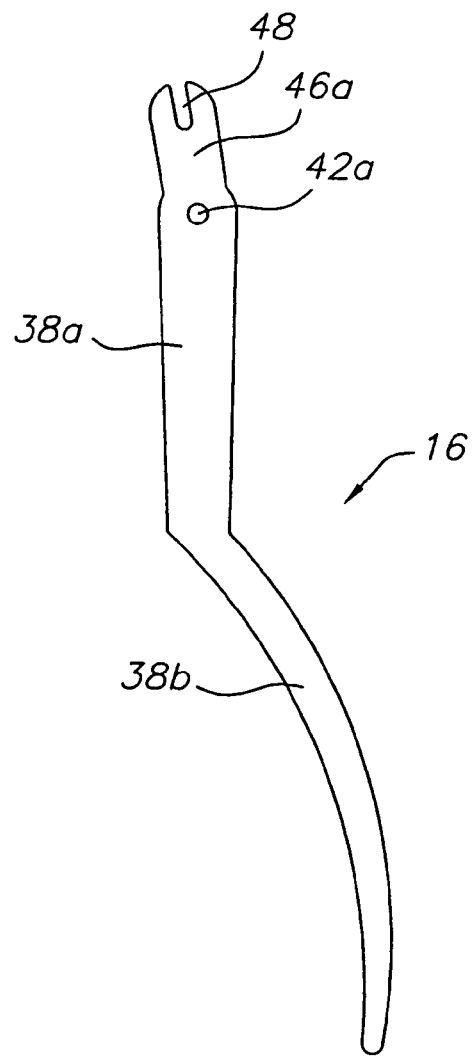
FIG. 5a is a side view of a pivot handle constructed in accordance with an exemplary embodiment of the invention.

In the embodiment shown, the pivot handle 16 extends generally downwardly from the cutting slide 14 and the elongated track member 12 and lies distal to the support handle 18. However, the pivot handle 16 may take any shape suitable for comfortably gripping both the support handle 18 and the pivot handle 16 with the same hand such that the pivot handle 18 can be squeezed toward the support handle 18. Preferably, as depicted in FIG. 5a, the pivot handle 16 has top and bottom ends and comprises a first grip segment 38a and a second grip segment 38b. The first grip segment 38a is located at the top end of the pivot handle 16 and is generally straight. The second grip segment 38b is located directly beneath the first grip segment 38a and is generally curved in the direction of the distal ends of the cutting slide 14 and track member 12.

Figure 5B:
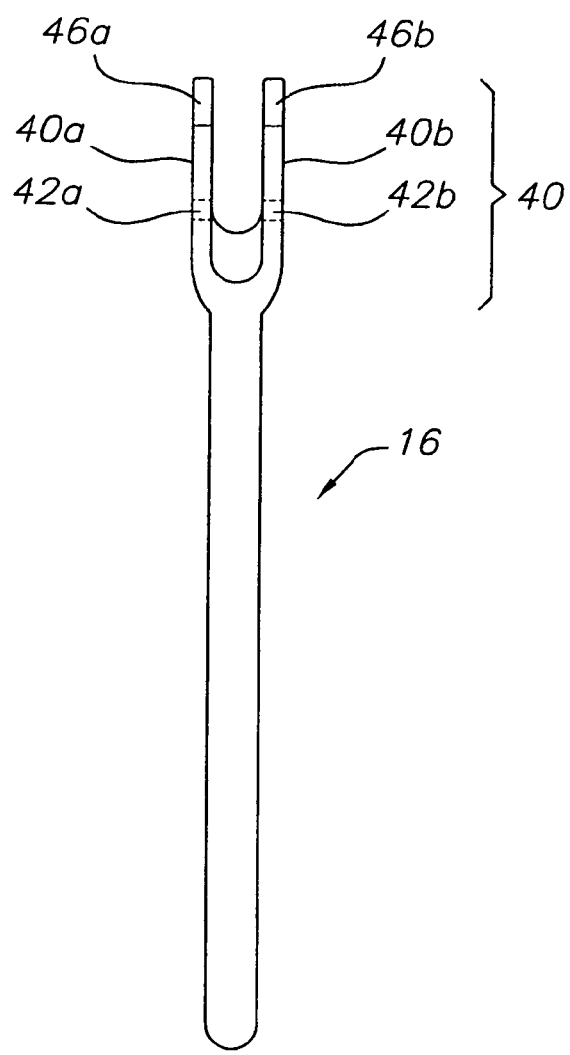
Figure 9A:
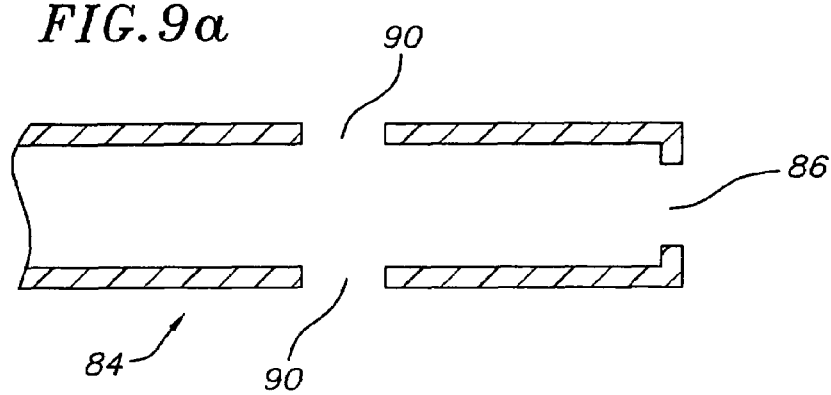
FIG. 9a is a longitudinal cross sectional view of a tubing of an alternative embodiment of a suction device according to an exemplary embodiment of the invention.
Figure 9B:
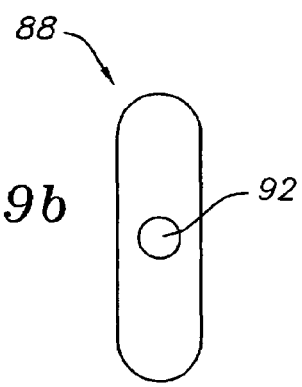
Figure 9C:
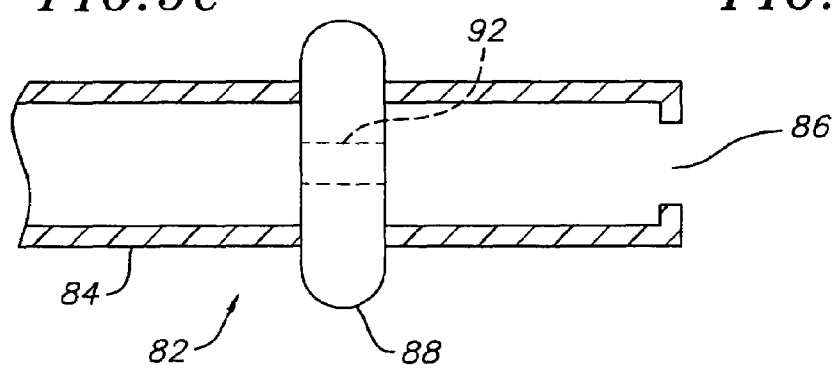
FIG. 9c is a longitudinal cross sectional view of the suction device depicted in FIGS. 9a and 9b in a venting configuration.
Figure 9D:
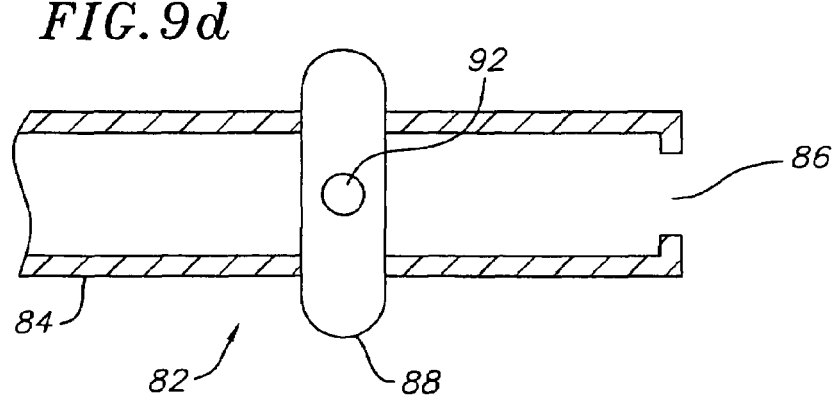
FIG. 9d is a longitudinal cross sectional view of the suction device depicted in FIGS. 9a and 9b in a suction configuration.

In the current embodiment, the top end of the pivot handle 14 terminates in a forked segment 40, as shown in FIG. 5b. The forked segment 40 comprises first and second prongs 40a and 40b, respectively, each prong having top and bottom ends. Slightly beneath the midpoint of the first prong 40a is an aperture 42a. Slightly beneath the midpoint of the second prong 40b is an internally threaded aperture 42b. The elongated track member 12 lies between the first and second prongs 40a and 40b of the forked segment 40. As shown, in the current embodiment, the apertures 42a and 42b are aligned with the aperture 30 in the elongated track member 12. A pivot pin 44 pivotally attaches the elongated track member 12 to the pivot handle 16. The pivot pin 44 passes through the aperture 42a in the first prong 40a, through the aperture 30 in the elongated track member 12, and into the aperture 42b of the second prong 40b. The pivot pin 44 has first and second ends, the first end carrying a screw head and the second end carrying external threading receivable by the internal threading of the aperture 42b of the second prong 40b.

The top end of the first prong 40a of the forked segment 40 carries a first extension member 46a. The top end of the second prong 40b of the forked segment 40 carries a second extension member 46b. Each of the extension members 46a and 46b include an elongated opening 48. When the apertures 40a and 40b are aligned with the aperture 30 in the elongated track member 12, the elongated openings 48 of each extension member 46a and 46b are aligned with the apertures 36 in the first and second side of the cutting slide 14.

The extension members 46a and 46b are attached to the cutting slide 14 preferably by a screw and bolt mechanism, as depicted in FIGS. 6a and 6b. The screw and bolt mechanism generally comprises a screw 50 and a bolt 52. The screw 50 comprises an elongated rod 54 having first and second ends, the second end terminating in a short section of external threading 56. The first end of the elongated rod 54 terminates in a first manually manipulable screw head 58. The bolt 52 comprises a second manually manipulable screw head 60 and a short neck member 62 having internal threading for receiving the external threading 56 on the second end of the screw 50. The elongated rod 52 of the screw 50 passes through the elongated opening 48 of the first extension member 46a, through the aperture 36 in the first side of the cutting slide 14, through the aperture 72 in the second side of the insertion tube 70 of the closure device 66, through the aperture 36 in the second side of the cutting slide 14, through the elongated opening 48 in the second extension member 46b, and into the bolt 52, where the external threading 56 on the second end of the screw 50 is received by the internal threading in the neck member 62 of the bolt 52.

The screw and bolt mechanism enables the easy removal of the cutting slide 14 from the elongated track member 12. To remove the cutting slide 14, the first and second track engaging protrusions 32a and 32b are aligned with the second and first slots 26b and 26a respectively, and the third track engaging protrusion 32c is positioned to lie outside the track 20. The screw and bolt mechanism is then removed by manually manipulating the first screw head 58 and the second screw head 60 and removing the elongated rod 54 of the screw 50 from the apertures in the cutting slide, extension members and closure device. Once the screw and bolt mechanism is removed, the cutting slide 14 is simply lifted out of the track 20. The bone fragments may then be removed from the inner cavity 80 of the cutting slide 14 by removing the closure device 66 and exposing the opening in the proximal end of the cutting slide 14.

Although specific methods of interconnecting the pivot handle 16, the cutting slide 14, and the extended track 12 have been shown and described above, it should be understood that any method of fixedly but removably interconnecting these pieces in a pivoting/sliding relationship one to the other may be utilized with the current invention.

Figure 1B:
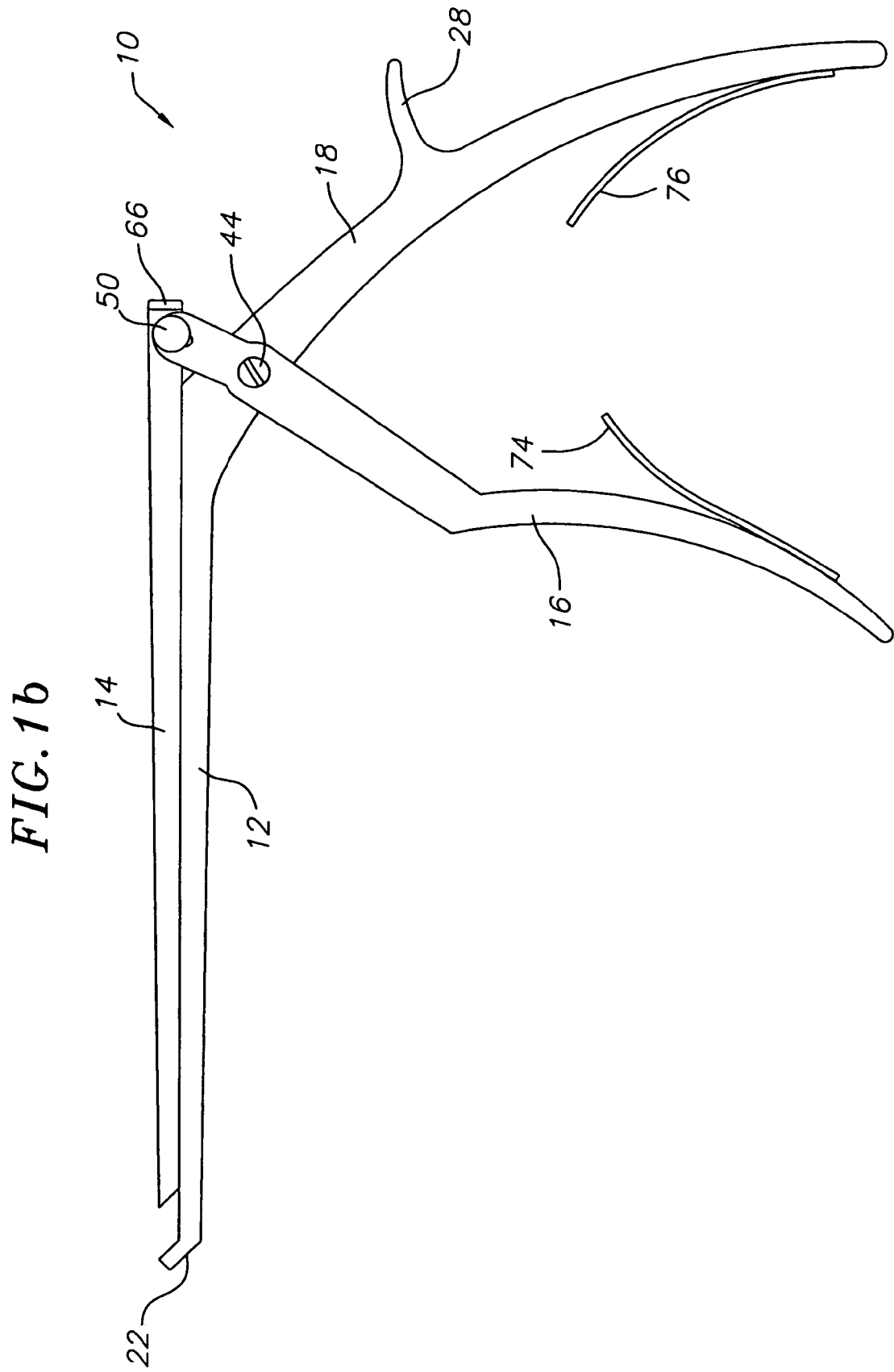
FIG. 1b is a side view of the surgical rongeur depicted in FIG. 1a in a second position.

As shown in FIGS. 1a and 1b, the pivot handle 16 and the support handle 18 may also be biased away from each other by spring members 74 and 76. In such an embodiment, each spring member 74 and 76 has top and bottom ends. The bottom end of spring member 74 is fixedly attached to the bottom end of the pivot handle 16. The bottom end of spring member 76 is fixedly attached to the bottom end of the support handle 18. The top ends of the spring members 74 and 76 include means to interlock the two spring members 74 and 76. When the spring members 74 and 76 are interlocked, they are biased away from each other, thereby biasing the pivot handle 16 distally. Any suitable means may be used to interlock the two spring members 74 and 76. For example, one spring member may include a protrusion at its top end that fits into a notch in the top end of the other spring member.

It should be understood that any suitable means for actuating the surgical rongeur can be used with this invention. The pivot handle and support handle described above are but one example of such actuating means. Also, the pivot handle and support handle described above may vary in dimension as desired.

During operation, longitudinal movement of the cutting slide 14 relative to the elongated track member 12 is effected by suitable manipulation of the pivot handle 16. The spring members 74 and 76 maintain the pivot handle 16 in a position biased away from the support handle 18 when a cut is not being performed. To perform a cut, the pivot handle 16 is squeezed toward the support handle 18. Squeezing the pivot handle 16 in this manner causes the cutting slide 14 to move distally relative to the elongated track member 12 until it reaches the second, closed position, whereby the sharp cutting edge 38 at the distal end of the cutting slide 14 cuts the bone that lies between the cutting edge 38 and the foot plate 22. Upon releasing pressure from the pivot handle 16, the spring members 74 and 76 cause the pivot handle 16 to return to its position biased away from the support handle 18. The spring members 74 and 76, by biasing the pivot handle 16 away from the support handle 18, thereby move the cutting slide 14 proximally relative to the elongated track member 12 until it reaches the first, open position, whereby another bone fragment may be placed between the sharp cutting edge 38 and the foot plate 22 in preparation for another cut.

As shown in FIGS. 1a and 1b, during operation, the cutting slide 14 is slidably received within the track 20 of the elongated track member 12. Accordingly, the cutting slide is longitudinally movable relative to the elongated track member 12. To cut bone against the foot plate 22, the cutting slide 14 is moved longitudinally from a first, open position (FIG. 1b) to a second, closed position (FIG. 1a). In the first position, as depicted in FIG. 1b, the cutting edge 38 is positioned proximal the foot plate 22 defining an opening between the cutting edge 38 and the foot plate 22. In preparation for a cut, the target bone is placed in the opening between the cutting edge 38 and the foot plate 22. In the second position, as depicted in FIG. 1a, the cutting edge 38 is in contact with the foot plate 22 of the elongated track member 12. In this closed position, the sharp cutting edge 38 is used to cut the bone against the foot plate 22.

As discussed, the proximal end of the cutting slide 14 also defines an opening (not shown). The opening in the proximal end of the cutting slide 14 enables the easy removal of cut bone chips from the inner cavity 80. Although the bone chips may be removed from the distal end, because the cross-sectional area of the cutting slide 14 is greatest at the proximal end, the bone chips will be easier to remove from the proximal end than from the distal end, which defines a smaller opening. However, as shown in FIGS. 7 and 6b, a closure device 66 may also be provided to close the proximal end of the cutting slide 14. The proximal end of the cutting slide 14 is preferably closed during any cutting procedure to ensure that the cut bone chips do not pass through the opening in the proximal end of the cutting slide 14 and fall back into the surgical situs.

FIG. 7 depicts the closure device 66, which generally comprises a cap member 68 and a short hollow insertion tube 70 having top and bottom ends, and first and second sides. The hollow insertion tube 70 is inserted into the inner cavity 80 of the cutting slide 14 through the opening in the proximal end of the cutting slide 14. When the insertion tube 70 is fully inserted, the cap member 68 closes the opening in the proximal end of the cutting slide 14. The hollow insertion tube 70 may be any length sufficient to ensure that the closure device 66 remains fixed to the proximal end of the cutting slide 14 during a cutting procedure. Preferably, the insertion tube 70 is of sufficient length such that when inserted into the inner cavity 80, it extends past the apertures 36 in the first and second sides of the cutting slide 14. Accordingly, the first and second sides of the insertion tube 70 include apertures 72 located near the bottom end of the insertion tube 70 which correspond to the apertures 36 in the cutting slide 14. When the insertion tube 70 is inserted into the inner cavity 80 of the cutting slide 14, the apertures 72 align with the apertures 36 in the first and second sides of the cutting slide 14. The apertures 72 in the insertion tube 70 allow passage of a connecting means through the aperture 36 in the first side of the cutting slide 14, through the aperture 72 in the first side of the insertion tube 70, through the aperture 72 in the second side of the insertion tube 70, and through the aperture 36 in the second side of the cutting slide 14. Any suitable connecting means may be used, such as a screw and bolt mechanism, as described above.

In an alternative embodiment shown in FIGS. 8a and 8b, a suction device may be attached to the proximal end of the cutting slide in place of the closure device. The suction device serves to enable the progression of soft tissue and ligament tissue toward the proximal end of the cutting slide. In addition, the suction device maintains soft tissue and ligament tissue within the jaws of the rongeur to enable cutting of those tissues. Without the suction device, cutting of these tissues is very difficult because the tissue tends to slip out of the cutting jaws before a cut is performed. However, suction must only be provided when the cutting jaws are closed. If suction is provided while the cutting jaws are open, nerves, e.g., may undesirably enter the cavity of the cutting slide.

Any device capable of providing suction force in the direction of the proximal end of the cutting slide may be used. For example, a suitable suction device utilizes negative atmospheric pressure to urge the soft tissue and ligament tissue through the cavity of the cutting slide. The suction device comprises a luer lock connection 81 attached to the proximal end of the cutting slide and a vent 83 disposed in the bottom surface 34 of the cutting slide 14. When the cutting jaws are open, and the vent 83 on the proximal end of the cutting slide 14 lies outside the track member 12, no suction is provided. However, when the cutting jaws are closed and the vent 83 is covered, suction is provided. The suction may be turned on and off by the luer lock connection 81. When the suction is turned on, suction is provided as described above. When the suction is turned off, no suction is provided regardless of the position of the cutting slide.

Another example of a suitable suction device 82 is shown in FIGS. 9a through 9d. The suction device 82 generally comprises a short section of tubing 84 having a hole 86 in its proximal end. A short rod 88 passes through two apertures 90 in the sides of the tubing 84. The rod 88 has a hole 92 through its center to facilitate the passage of air. When suction is not needed the rod 88 is rotated such that the hole 92 through its center is aligned with the hole 86 at the proximal end of the tubing 84. In this configuration, shown in FIG. 9c, the suction device 82 merely vents, providing no suction force. When suction is needed to aid the progression of soft tissue or ligament tissue toward the proximal end of the cutting slide, the rod 88 is rotated such that the hole 92 is not aligned with the hole 86 in the tubing 84. In this configuration, shown in FIG. 9d, the solid part of the center of the rod 88 is aligned with the hole 86 in the tubing 84, thereby providing suction force within the cavity of the cutting slide.

Each element of the surgical rongeur according to this invention may be made of any suitable material, such as metal, plastic, ceramic or composite material. However, the sharp cutting edge 38 at the distal end of the cutting slide 14 should be made of a material that is sufficiently sharp to cut bone or tissue, such as metal, ceramic or composite material.

In addition, the size of the surgical rongeur may vary as desired, and differently sized rongeurs may be used to cut differently sized bone fragments. Also, as described above, the foot plate 22 at the distal end of the track member 12 may be either perpendicular to, or angled relative to, the track member 12. The size of the replaceable cutting slide 14 will therefore vary with the varying sizes of the rongeurs, as well as with the angle of the foot plate 22. In order to ensure that a user does not replace the cutting slide 14 of a rongeur with another cutting slide of the wrong size, it is preferred that the parts of each rongeur be color-coded. For example, a rongeur having a foot plate angled 45° from the track member may be colored blue, while a rongeur having a foot plate extending perpendicularly to the track member may be colored red. In addition, rongeurs of varying sizes may be coded with different colors.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. Accordingly, the foregoing description should not be read as pertaining only to the precise embodiments described, but rather should be read consistent with and as support for the following claims which are to have their fullest and fairest scope.

What is claimed is:

1. A surgical rongeur for cutting bone or tissue comprising:
    an elongated track member having proximal and distal ends, the distal end terminating in a foot plate;
    an elongated cutting slide in a sliding arrangement with the elongated track member, the cutting slide having proximal and distal ends, first and second sides, and top and bottom surfaces defining an inner cavity, the distal end of the cutting slide defining a sharp cutting edge and an opening through which access is granted to the inner cavity, wherein the cutting slide is removably received within the elongated track member such that the sharp cutting edge may engage the foot plate, wherein the cutting slide further comprises an opening at its proximal end, and a closure device for removably closing the opening in the proximal end of the cutting slide; and
    means for slidably moving the cutting slide longitudinally relative to the elongated track member.

2. A surgical rongeur according to claim 1, wherein the closure device for removably closing the opening in the proximal end of the cutting slide comprises a closure device comprising a cap member and a short generally hollow insertion tube, wherein the insertion tube is inserted into the inner cavity of the cutting slide through the opening in the proximal end of the cutting slide.

3. A surgical rongeur according to claim 1, wherein the means for moving the cutting slide longitudinally relative to the track member comprises:
    a support handle extending downwardly from the proximal end of the track member; and
    a pivot handle removably attached to the cutting slide and pivotally attached to the support handle
    wherein manipulation of the pivot handle slidably moves the cutting slide along the track member from a first open position in which the sharp cutting edge is positioned proximal. the foot plate defining an opening between the sharp cutting edge and the foot plate, and a second closed position in which the sharp cutting edge is in contact with the foot plate.

4. A surgical rongeur according to claim 1, wherein the elongated track member further comprises a track for slidably receiving the cutting slide, the track extending substantially the length of the elongated track member.

5. A surgical rongeur according to claim 4, wherein the track comprises an elongated narrow groove.

6. A surgical rongeur according to claim 4, wherein the cutting slide further comprises at least one track engaging protrusion for engaging the track in the elongated track member.

7. A surgical rongeur according to claim 6, wherein the track further comprises at least one slot having a width slightly greater than a width of the narrow groove, the at least one slot arranged to allow the removable insertion of the protrusion into the narrow groove.

8. surgical rongeur according to claim 5, wherein the track further comprises:
    a first slot near the proximal end of the elongated track member; and
    a second slot near the distal end of the elongated track member;
    wherein the first and second slots each have widths greater than a width of the elongated narrow groove of the track.

9. A surgical rongeur according to claim 8, wherein the cutting slide further comprises:
    a first track engaging protrusion at the distal end of the cutting slide having a length slightly smaller than a length of the second slot of the track;
    a second track engaging protrusion near a midpoint of the cutting slide having a length slightly smaller than a length of the first slot of the track; and a third track engaging protrusion at the proximal end of the cutting slide having a length such that when the first track engaging protrusion is aligned with the second slot of the track and the second track engaging protrusion is aligned with the first slot of the track, the third track engaging protrusion lies completely outside the track.

10. A surgical rongeur according to claim 1, wherein the generally hollow cutting slide increases in cross-sectional area from its distal end to its proximal end.

11. A surgical rongeur according to claim 6, wherein the elongated narrow groove of the track is generally T-shaped, and the at least one track engaging protrusion of the cutting slide is generally T-shaped for engaging the generally T-shaped groove in the track.

12. A surgical rongeur according to claim 9, wherein the elongated narrow groove of the track is generally T-shaped, and the first, second and third track engaging protrusions of the cutting slide are generally T-shaped for engaging the generally T-shaped groove in the track.

13. A surgical rongeur according to claim 3, wherein the pivot handle comprises top and bottom ends, the top end terminating in a forked segment, the forked segment comprising:
   a first prong carrying a first aperture and terminating in a first extension member, the first extension member defining a first elongated opening; and
   a second prong carrying a second aperture and terminating in a second extension member, the second extension member defining a second elongated opening;
   wherein the elongated track member lies between the first and second prongs of the pivot handle, the prongs being pivotally connected to the elongated track member and removably connected to the cutting slide.

14. A surgical rongeur according to claim 13, further comprising:
   means for pivotally connecting the pivot handle to the support handle; and
   means for removably connecting the forked segment of the pivot handle to the proximal end of the cutting slide.

15. A surgical rongeur according to claim 14, wherein the cutting slide further comprises a first aperture in its first side, and a second aperture in its second side, the first and second apertures being located near the proximal end of the cutting slide, and further wherein the means for removably connecting the forked segment of the pivot handle to the proximal end of the cutting slide comprises:
   a screw comprising an elongated rod having first and second ends, the first end terminating in a first manually manipulable screw head, the second end terminating in a short section of external threading; and
   a bolt comprising a second manually manipulable screw head and a neck member having internal threading for receiving the short section of external threading on the screw;
   wherein the elongated rod of the screw extends through the first elongated opening in the first extension member, through the first aperture in the first side of the cutting slide, through the second aperture in the second side of the cutting slide, through the second elongated opening in the second extension member, and into the internally threaded neck member of the bolt.

16. A surgical rongeur according to claim 1, wherein the rongeur is easily disassembled by removing the cutting slide from the track member.

17. A surgical rongeur according to claim 1, further comprising a suction device mounted at the proximal end of the cutting slide.

18. A surgical rongeur according to claim 17, wherein the suction device comprises:
   a short tubing having a proximal end, two apertures through a center of the tubing and a hole in the proximal end of the tubing; and
   a short rod passing through the two apertures in the tubing, the rod having a hole through its center.

19. A surgical rongeur according to claim 18, wherein when the rod is rotated such that the hole through the rod is aligned with the hole in the proximal end of the tubing, air is allowed to vent through the cutting slide.

20. A surgical rongeur according to claim 18, wherein when the rod is rotated such that a solid part of the rod is aligned with the hole in the proximal end of the tubing, suction force is applied through the cavity of the cutting slide.

21. A surgical rongeur according to claim 17, wherein the suction device comprises a vent on the bottom surface of the cutting slide, wherein suction is provided when the proximal side of the cutting slide lies outside the track member, and wherein suction is not provided when the proximal side of the cutting slide lies within the track member.

22. A surgical rongeur according to claim 21, wherein the suction device further comprises means for turning suction on and off.

23. A surgical rongeur according to claim 22, wherein the means for turning suction on and off comprises a luer lock connection.

24. A surgical rongeur for cutting bone or tissue comprising:
   an elongated track member having proximal and distal ends, the distal end terminating in a foot plate, the proximal end terminating in a support handle having top and bottom ends and extending downwardly from the track member, the elongated track member further comprising a track extending substantially the length of the elongated track member;
   an elongated cutting slide in a sliding arrangement with the elongated track member, the cutting slide having proximal and distal ends, first and second sides, and top and bottom surfaces defining an inner cavity, the distal. end of the cutting slide defining a sharp cutting edge and an opening through which access is granted to the inner cavity, wherein the cutting slide is removably received within the elongated track member such that the sharp cutting edge may engage the foot plate, the cutting slide further comprising at least one track engaging protrusion extending downwardly from the bottom surface of the cutting slide for engaging the track of the elongated track member, wherein the cutting slide further comprises an opening at its proximal end, and a closure device for removably closing the opening in the proximal end of the cutting slide;
   a pivot handle having top and bottom ends extending downwardly from the elongated track member;
   means for pivotally attaching the pivot handle to the support handle; and
   means for removably attaching the pivot handle to the proximal end of the cutting slide;
   wherein manipulation of the pivot handle slidably moves the cutting slide longitudinally relative to the track member from a first open position in which the sharp cutting edge of the cutting slide is positioned proximal the foot plate defining an opening between the sharp cutting edge and the foot plate, and a second closed position in which the sharp cutting edge is in contact with the foot plate.

25. A surgical rongeur according to claim 24, wherein the closure device for removably closing the opening in the proximal end of the cutting slide comprises a closure device comprising a cap member and a short generally hollow insertion tube, wherein the insertion tube is inserted into the inner cavity of the cutting slide through the opening in the proximal end of the cutting slide.

26. A surgical rongeur according to claim 24, wherein the track comprises an elongated narrow groove.

27. A surgical rongeur according to claim 26, wherein the track further comprises at least one slot having a width slightly greater than a width of the narrow groove, the at least one slot arranged to allow the removable insertion of the protrusion in to the narrow groove.

28. A surgical rongeur according to claim 26, wherein the track further comprises:
 a first slot near the proximal end of the elongated track member; and
 a second slot near the distal end of the elongated track member;
 wherein the first and second slots each have widths greater than a width of the elongated narrow groove of the track.

29. A surgical rongeur according to claim 28, wherein the cutting slide comprises:
 a first track engaging protrusion at the distal end of the cutting slide having a length slightly smaller than a length of the second slot of the track;
 a second track engaging protrusion near a midpoint of the cutting slide having a length slightly smaller than a length of the first slot of the track; and
 a third track engaging protrusion at the proximal end of the cutting slide having a length such that when the first track engaging protrusion is aligned with the second slot of the track and the second track engaging protrusion is aligned with the first slot of the track, the third track engaging protrusion lies completely outside the track.

30. A surgical rongeur according to claim 24, wherein the cutting slide increases in cross-sectional area from its distal end to its proximal end.

31. A surgical rongeur according to claim 26, wherein the elongated narrow groove of the track is generally T-shaped, and the at least one track engaging protrusion of the cutting slide is generally T-shaped for engaging the generally T-shaped groove in the track.

32. A surgical rongeur according to claim 29, wherein the elongated narrow groove of the track is generally T-shaped, and the first, second and third track engaging protrusions are generally T-shaped for engaging the generally T-shaped groove in the track.

33. A surgical rongeur according to claim 24, wherein the top end of the pivot handle terminates in a forked segment, the forked segment comprising:
 a first prong carrying a first aperture and terminating in a first extension member, the first extension member defining a first elongated opening; and
 a second prong carrying a second aperture and terminating in a second extension member, the second extension member defining a second elongated opening;
 wherein the elongated track member lies between the first and second prongs of the pivot handle, the prongs being pivotally connected to the elongated track member and removably connected to the cutting slide.

34. A surgical rongeur according to claim 32, wherein the cutting slide further comprises a first aperture in its first side, and a second aperture in its second side, the first and second apertures being located near the proximal end of the cutting slide, and further wherein the means for removably attaching the pivot handle to the cutting slide comprises:
 a screw comprising an elongated rod having first and second ends, the first end terminating in a first manually manipulable screw head, the second end terminating in a short section of external threading; and
 a bolt comprising a second manually manipulable screw head and a neck member having internal threading for receiving the short section of external threading on the screw;
 wherein the elongated rod of the screw extends through the first elongated opening of the first extension member, through the first aperture in the first side of the cutting slide, through the second aperture in the second side of the cutting slide, through the second elongated opening in the second extension member, and into the internally threaded neck member of the bolt.

35. A surgical rongeur according to claim 24, wherein the rongeur is easily disassembled by removing the cutting slide from the track member.

* * * * *

UNITED STATES PATENT AND TRADEMARK OFFICE
CERTIFICATE OF CORRECTION

| | |
|---|---|
| PATENT NO. | : 7,615,053 B2 |
| APPLICATION NO. | : 11/005058 |
| DATED | : November 10, 2009 |
| INVENTOR(S) | : Laurence M. McKinley |

Page 1 of 1

It is certified that error appears in the above-identified patent and that said Letters Patent is hereby corrected as shown below:

Col. 10, Claim 3, line 32, delete "." after proximal and add --to--.
    Col. 12, Claim 24, line 40, after the word distal delete ".".

Signed and Sealed this
Twenty-sixth Day of February, 2013

Teresa Stanek Rea
*Acting Director of the United States Patent and Trademark Office*